US010734111B2

(12) United States Patent
Vinod et al.

(10) Patent No.: US 10,734,111 B2
(45) Date of Patent: Aug. 4, 2020

(54) METHOD AND ARRANGEMENT FOR DETERMINING A QUALITY RATING DATA FOR A MEDICAL DATA ACQUISITION SYSTEM

(71) Applicant: KONINKLIJKE PHILIPS N.V., Eindhoven (NL)

(72) Inventors: Kishore Vinod, Bangalore (IN); Cornelis Jacobus Hendrikus Adrianus Blom, Eindhoven (NL); Prashanth Pai, Bothell, WA (US); Santosh Yalawar, Bangalore (IN); Paul Derckx, Best (NL); Franciscus Johannes Maria Benschop, Best (NL); Vinay Parthan, Best (NL)

(73) Assignee: Koninkliljke Philips N.V., Eindhoven (NL)

( * ) Notice: Subject to any disclaimer, the term of this patent is extended or adjusted under 35 U.S.C. 154(b) by 375 days.

(21) Appl. No.: 15/537,903

(22) PCT Filed: Dec. 15, 2015

(86) PCT No.: PCT/IB2015/059608
§ 371 (c)(1),
(2) Date: Jun. 20, 2017

(87) PCT Pub. No.: WO2016/103106
PCT Pub. Date: Jun. 30, 2016

(65) Prior Publication Data
US 2018/0004906 A1    Jan. 4, 2018

(30) Foreign Application Priority Data
Dec. 22, 2014    (IN) .......................... 6457/CHE/2014

(51) Int. Cl.
*G06F 11/00* (2006.01)
*G16H 40/40* (2018.01)
*G06Q 10/00* (2012.01)

(52) U.S. Cl.
CPC ............. *G16H 40/40* (2018.01); *G06Q 10/00* (2013.01); *G06F 11/00* (2013.01)

(58) Field of Classification Search
CPC ......... G16H 40/40; G06Q 10/00; G06F 11/00
See application file for complete search history.

(56) References Cited

U.S. PATENT DOCUMENTS

| 7,398,132 B2 | 7/2008 | Steinhilper | |
| 8,270,748 B1 * | 9/2012 | Silver | ................... G06K 9/481 382/254 |

(Continued)

OTHER PUBLICATIONS

Andrew F. Hayes et al: "Answering the Call for a Standard Reliability Measure for Coding Data", Communication Methods and Measures, vol. 1, No. 1, Apr. 1, 2007 (Apr. 1, 2007), pp. 77-89.

(Continued)

*Primary Examiner* — Mohammad K Islam

(57) ABSTRACT

A method for determining a quality rating data (QRD) of a medical data acquisition system (MDAS) includes receiving first data which includes utilization errors by an MDAS that occurred while performing a data acquisition procedure (DAP), by a data acquisition component of the MDAS, to acquire medical data. The method also includes generating second data as a function of the first data, the second data being indicative of categories of the utilization errors, wherein at least one utilization error is assigned to a corresponding category based on a predetermined parameter. The method further includes determining the quality rating data as a function of a total number of MDAS utilizations, a corresponding coefficient for the corresponding utilization (Continued)

error category and a number of utilization errors in the corresponding error category.

20 Claims, 6 Drawing Sheets

(56) References Cited

U.S. PATENT DOCUMENTS

| | | | | |
|---|---|---|---|---|
| 8,423,113 | B2* | 4/2013 | Shariati | A61B 5/14532 600/345 |
| 2006/0188004 | A1 | 8/2006 | Kizu et al. | |
| 2007/0118399 | A1* | 5/2007 | Avinash | G16H 10/60 705/2 |
| 2008/0103834 | A1* | 5/2008 | Reiner | G16H 70/20 705/3 |
| 2008/0132770 | A1 | 6/2008 | Ayers et al. | |
| 2008/0230705 | A1* | 9/2008 | Rousso | A61B 5/415 250/363.04 |
| 2010/0205485 | A1* | 8/2010 | Tashiro | H04L 41/5035 714/37 |
| 2011/0213211 | A1* | 9/2011 | Stevens | G06Q 10/00 600/300 |
| 2011/0276346 | A1* | 11/2011 | Reiner | G06Q 50/22 705/3 |
| 2012/0108910 | A1 | 5/2012 | Berkane et al. | |
| 2012/0191383 | A1 | 7/2012 | Huff et al. | |
| 2012/0253847 | A1* | 10/2012 | Dell'Anno | A61B 5/0022 705/3 |
| 2013/0231947 | A1* | 9/2013 | Shusterman | G06F 19/3418 705/2 |
| 2014/0153808 | A1* | 6/2014 | Wu | G06F 19/321 382/131 |
| 2016/0338613 | A1* | 11/2016 | Beckers | G06F 19/321 |
| 2017/0032281 | A1* | 2/2017 | Hsu | B23K 9/0953 |
| 2017/0323054 | A1* | 11/2017 | Johansson | G06F 19/321 |
| 2017/0366596 | A1* | 12/2017 | Han | H04L 1/0006 |
| 2019/0171714 | A1* | 6/2019 | Gale | G06F 16/335 |

OTHER PUBLICATIONS

Ching-Seh Wu et al: "Optimizing Medical Data Quality Based on Multiagent Web Service Framework",IEEE Transactions on Information Technology in Biomedicine, IEEE Service Center, Los Alamitos, CA, US,vol. 16, No. 4, Jul. 1, 2012 (Jul. 1, 2012),pp. 745-757.

Johns, M.V., "Reliabilty Assessment for Highly Reliable Systems" Techincal Report No. 1, US Army Research Office, Nov. 15, 1975.

Robin A. Felder et al "Process Evaluation of a Fully Automated Molecular Diagnostics System" Journal of Laboratory Automation, 2009, 14: 252-268.

Teledyne Application Notes, 2010.

Chao et al "Application of Simulated Technology in Reliability Measure of Ad Hoc Network" Maintenance and Reliability, issue 2, (46) 2010 p. 27-30.

* cited by examiner

Operational Data
600

| SRN | Utilization Error | Time/Date Stamp | Technician ID | Environmental Data |
|---|---|---|---|---|
| 601 | 602 | 603 | 604 | 605 |

METHOD AND ARRANGEMENT FOR DETERMINING A QUALITY RATING DATA FOR A MEDICAL DATA ACQUISITION SYSTEM

CROSS REFERENCE TO RELATED APPLICATIONS

This application is a U.S. national phase application of International Application No. PCT/IB2015/059608, filed on Dec. 15, 2015, which claims the benefit of International Application Serial No. 6457/CHE/2014 filed on Dec. 22, 2014 and is incorporated herein by reference.

A medical institution may have a plurality of Medical Data Acquisition Systems (MDAS) configured to generate medical data corresponding to various medical procedures. For example, the MDAS may be an imaging device used to visualize internal structures of a body. For example, the imaging device may be a Magnetic Resonance Imaging (MRI) device. The data gathered from using this technique may provide a basis in which an anatomical image may be generated. Specifically, a cross sectional, axial image of internal structures of the body may be represented in a two-dimensional image or more complex images may be generated as a three-dimensional image. In this manner, a non-invasive, no-dose modality for imaging soft tissue is provided. The image may be used by a user such as a physician, technician, etc. to determine whether the internal structures captured in the image are healthy, injured, etc. from determining whether any anomalies are present. As such, the imaging device is complex and may experience a variety of problems and failures.

The clinical examination of a patient using the MDAS means time and money for both the patient and the hospital and hence the conditions leading to failures of starting up a scan, the scan itself, and the post processing of the images acquired from the scan are studied critically. The failure of exam equipment can lead to the loss of the customer (e.g. hospital) and may lead to equipment service costs running to thousands of dollars. Therefore, reliability metrics are used to determine the dependability of the MDAS.

Reliability metrics like Mean Time Between Failures (MTBF) and Mean Time Between Crashes (MTBC) are operational metrics measured in terms of the failure over time. Other metrics like B10 life (L10) look into the failures of electro-mechanical components and may have little to do with software. This again is a time-based metric that determines the time taken for 10% of the population of a product to fail. Since both these metrics deal with the time and indicate optimum operable limits, it is not clear if the system can survive this limit and/or exceed in performing capacity.

Accordingly, it is desirable to determine a reliability metric in terms of the clinical exam performed and independent of time.

The exemplary embodiments relate to a method and arrangement for determining a quality rating data (QRD) for a medical data acquisition system (MDAS).

According to an aspect of the present disclosure, the method comprises receiving first data, which includes utilization errors occurred during performing a data acquisition procedure (DAP), by a data acquisition component of the MDAS, on a patient to acquire medical data. The method further comprises determining second data as a function of the first data. The second data is indicative of categories of the utilization errors, wherein at least one utilization error is assigned to a corresponding category based on a predetermined parameter. The method further comprises determining the QRD as a function of a total number of MDAS utilizations, a predetermined coefficient for the corresponding error category and a number of utilization errors in the corresponding error category.

In another aspect, the QRD is determined according to the following:

$$QRD = \frac{N}{\sum_{n=1}^{k} F_n L_n + F_{n+1} L_{n+1} + \ldots + F_k L_k}$$

wherein, N is the total number of the MDAS utilizations, $F_n$ is the coefficient corresponding to the utilization error categories, $L_n$ is a number of utilization errors in the error category, and k is a total number of the utilization error categories.

In another aspect, the MDAS includes one of a magnetic resonance imagining (MRI) device, a computed tomography (CT) device, an ultrasound device, an X-ray device, and a nuclear magnetic resonance (NMR) device.

In another aspect, the utilization error categories includes at least one of a category L1, which contains fatal utilization errors, a category L2, which contains major utilization errors, a category L3, which contains recoverable utilization errors, and a category L4, which contains minor utilization errors.

In another aspect, the corresponding coefficient of $F_1$ is 0.5, the corresponding coefficient of $F_2$ is 0.35, the corresponding coefficient of $F_3$ is 0.01, and the corresponding coefficient of $F_4$ is 0.006.

In another aspect, the first data further includes at least one of a serial reference number (SRN) of the data acquisition component or the MDAS, a time/date stamp of the utilization error that occurred during the DAP, an identification number of a technician who performed the DAP using the MDAS, and environmental data of the data acquisition component during the DAP at a time/date of the utilization error.

In another aspect, the method further comprises determining a corresponding action as a function of the QRD.

In a further aspect, the corresponding action includes at least one of transmitting instructions to the MDAS, remotely shutting down the data acquisition component, issuing a maintenance recommendation, rebooting the MDAS, recommending repositioning the patient, scheduling a maintenance, recommending a replacement of the data acquisition component, running a diagnostic test on the data acquisition component, and adjusting components of the data acquisition component.

In another aspect, the receiving further includes utilizing a data mining process to retrieve the first data.

In another aspect, the corresponding coefficient includes being determined by utilizing a neural network type computational model.

Figure 1:
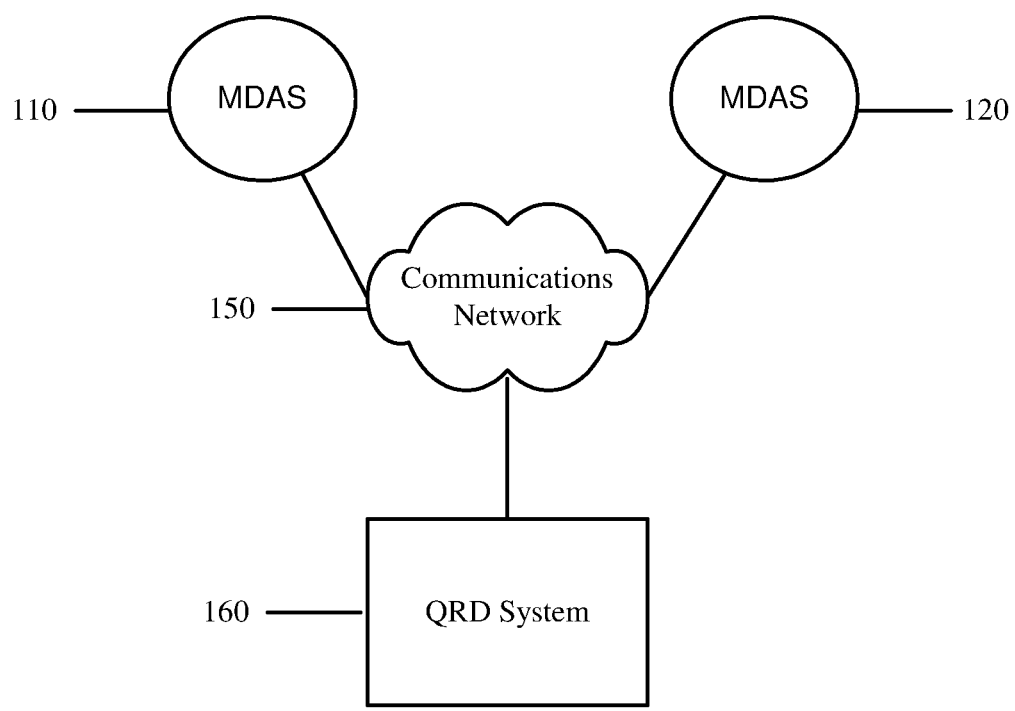
FIG. 1 shows a health care service system, according to exemplary embodiments.

The exemplary embodiments may be further understood with reference to the following description of the exemplary embodiments and the related appended drawings, wherein like elements are provided with the same reference numerals. The exemplary embodiments are related to a method and arrangement of determining a Quality Ranking Data (QRD). Specifically, the exemplary embodiments can implement the method and arrangement with reference to a Medical Data Acquisition System (MDAS). As will be described in greater detail below, the QRD may be used as a reliability metric to evaluate and compare a performance of the MDASs. It should be noted that the exemplary embodiments will make reference to a user. The user may include, but it is not limited to, a MDAS technician, a doctor or other persons capable of utilizing the MDAS.

FIG. 1 shows a health care service system 100 according to exemplary embodiments. One of the services of the health care service system 100 is to acquire medical data relating to a patient. For example, the patient may require an imaging scan to be performed on a specific body portion. The system 100 includes at least one MDAS 110, a communications network 150 and a QRD System 160.

The MDAS 110 is utilized to perform a data acquisition procedure (DAP) to generate the medical data of the patient. During the DAP, other data will also be generated. One skilled in the art would understand that the system 100 may include a plurality of MDASs 110, 120.

The communications network 150 is used to assist in communication between the MDAS 110 and the QRD System 160. According to the exemplary embodiments, the communications network 150 may be a network environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art would appreciate that such network computing environments typically encompass many types of computer systems configurations, including personal computers, hand-held devices, multi-processor systems, microprocessor-based or programmable consumer electronics, network PCs, minicomputers, mainframe computers, and the like. Exemplary embodiments of the invention may also be practiced in distributed computing environments where tasks are performed by local and remote processing devices that are linked (either by hardwired links, wireless links or by a combination of hardwired or wireless links) through a communications network. In a distributed computing environment, program modules may be located in both local and remote memory storage devices.

The QRD System 160 is utilized to generate the QRD based on data provided by the MDAS 110 and other data provided by third parties, such as manufacturer's data and historic data. The QRD System 160 may further control specific aspects of the MDAS 110 based on the QRD.

Figure 2:
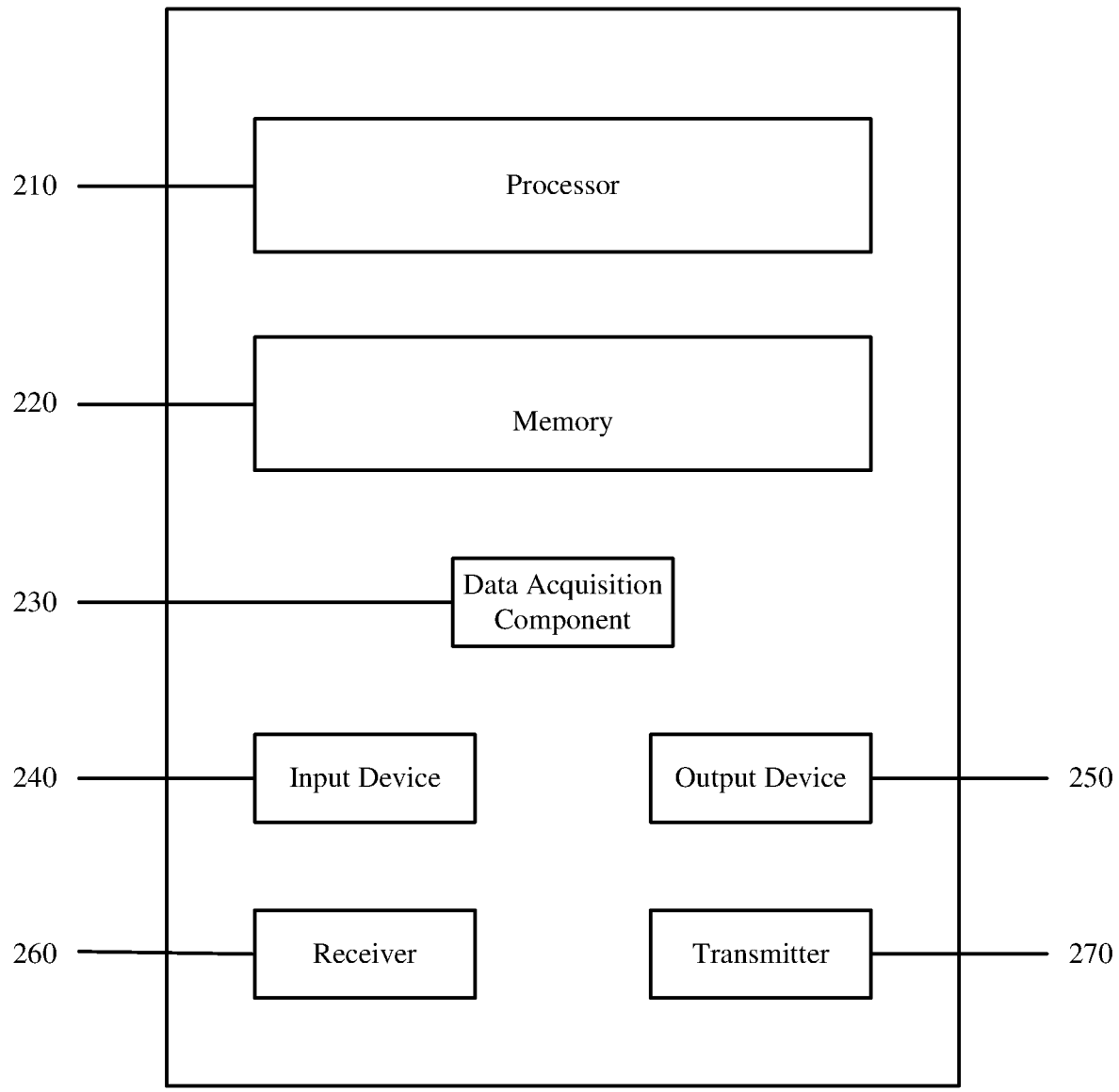
FIG. 2 shows the MDAS, according to exemplary embodiments.

FIG. 2 shows the MDAS 110 according to exemplary embodiments. The MDAS 110 includes a processor 210, a memory 220, a data acquisition component 230, an input device 240, an output device 250, a receiver 260 and a transmitter 270.

The data acquisition component 230 is a component which generates the medical data of the patient. The data acquisition component 230 may include, but is not limited to, a Magnetic Resonance Imaging (MRI) device, a computed topography (CT) device, an ultrasound machine, an X-Ray device, a Nuclear Magnetic Resonance (NMR) device and others. Although the exemplary system and methods may be applied to any data acquisition component 230, exemplary embodiments will make reference to an MRI device.

The processor 210 may engage the data acquisition component 230 to perform the DAP, as well as engage other components of the MDAS 110. The memory 220 stores patients' medical data as well as other data relating to the DAP and the data acquisition component 230.

The input device 240 may receive inputs from the user and includes a keyboard, a mouse, a touch screen and/or other input devices. The output device 250 may communicate data to the user via a monitor, a printer and/or other output devices. The receiver 260 and the transmitter 270 may be utilized for wired and/or wireless communications such as with the communications network 150. In an exemplary embodiment, the MDAS 110 may include a combined transceiver to provide the functionalities of the receiver 260 and transmitter 270.

Figure 3:
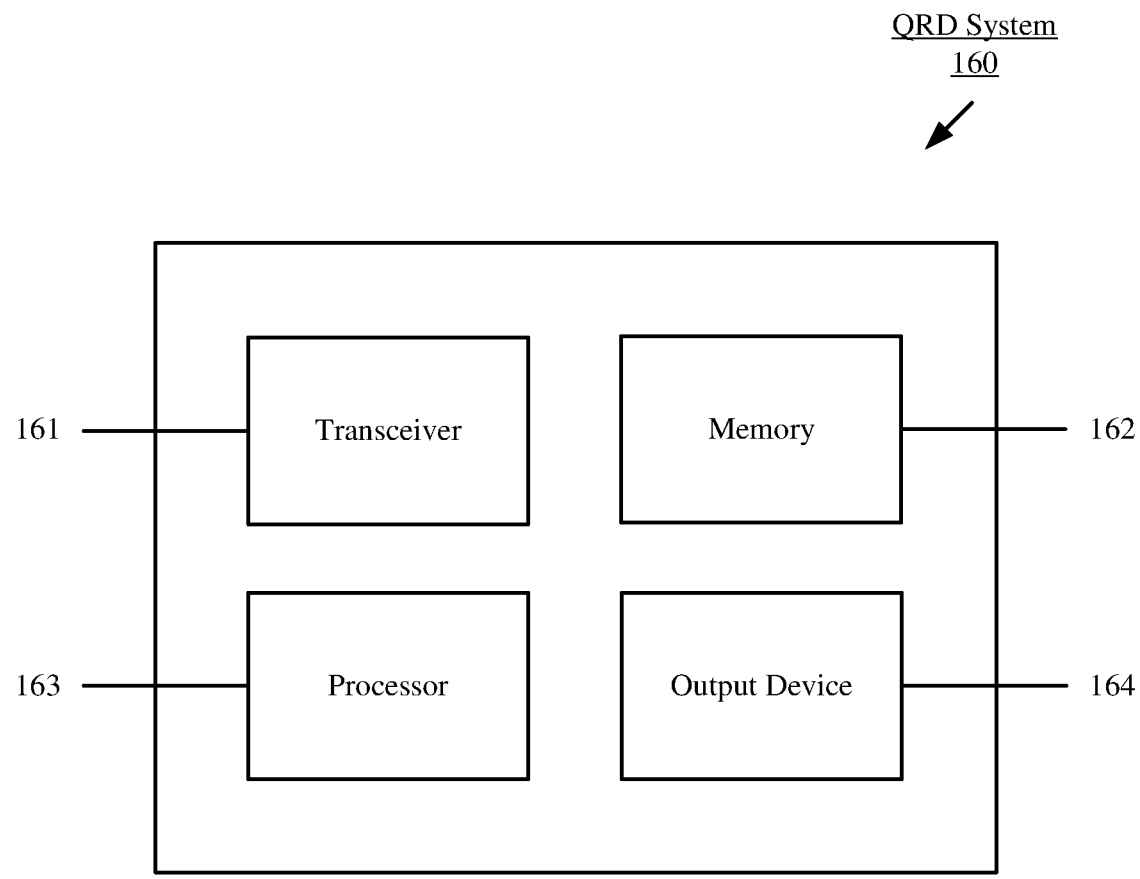
FIG. 3 shows a QRD System, according to exemplary embodiments.

FIG. 3 shows the QRD System 160 of FIG. 1 according to exemplary embodiments. The QRD System 160 includes a transceiver 161, a memory 162, a processor 163, and an output device 164. As discussed above, the QRD System 160 may be configured to communicate, via the communications network 150, with the MDAS 110.

The processor 163 may engage the transceiver 161 to communicate with the MDAS 110. The memory 162 stores data received from the MDAS 110 as well as other data and programs necessary to operate the QRD System 160. The memory 162 may also store received data from a plurality of third parties. The processor 163 may also determine the QRD. In an exemplary embodiment, the processor 163 may control specific functions of the MDAS 110 based on the QRD. The output 164 may output the QRD on a monitor, a printer and/or other output devices.

Figure 4:
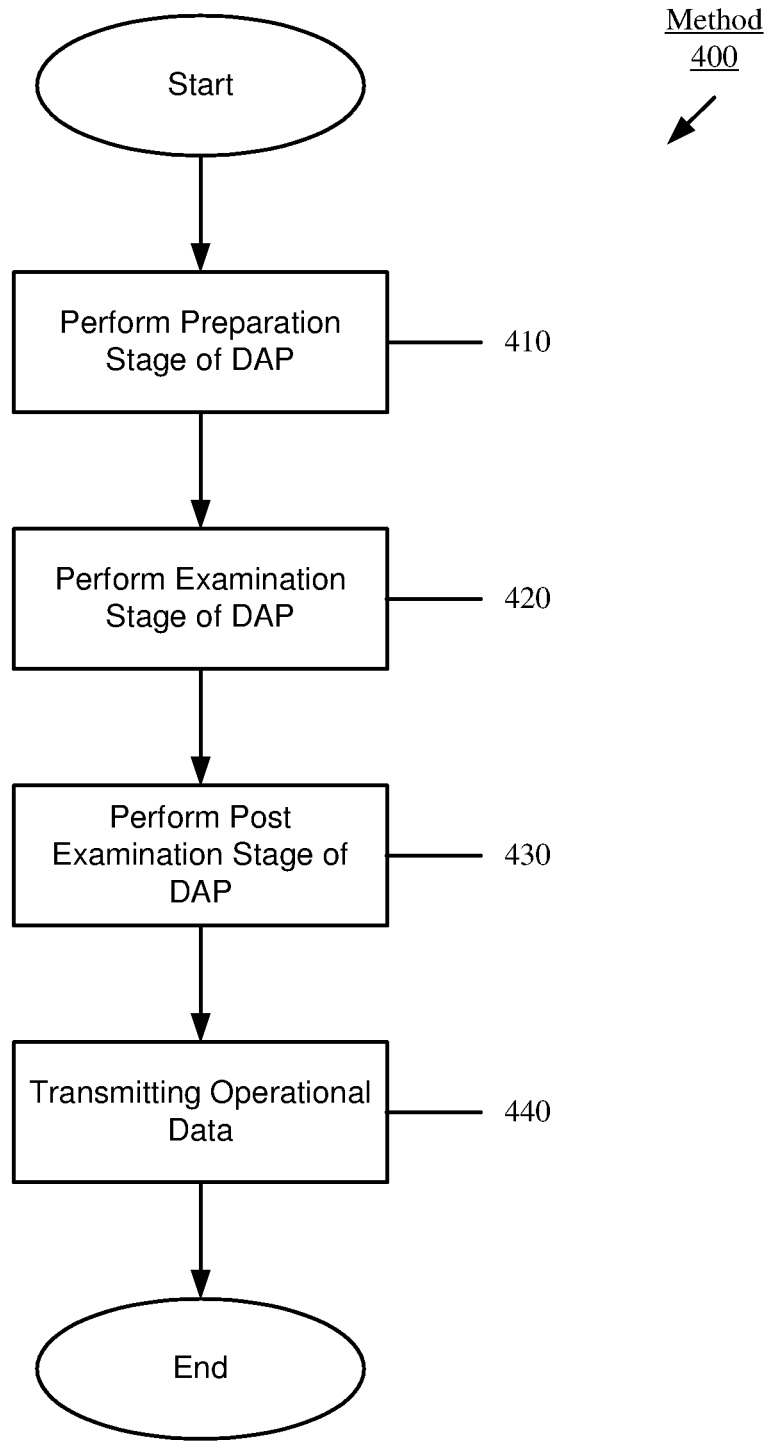
FIG. 4 shows a method for recording and transmitting operational data, according to exemplary embodiments.

FIG. 4 shows the method 400 for generating and transmitting operational data (e.g. first data) 600, according to exemplary embodiments. The operational data 600 can include various data collected regarding the DAP and will be described in greater detail below. The method 400 will be described with regards to the health care service system 100 of FIG. 1.

In step 410, the user performs a preparation stage of the DAP by conducting a system start up and booting up the data acquisition component 230. Once the system start up is finished, a system setup may commence to calibrate the data acquisition component 230.

In step 420, the user performs an examination stage of the DAP. Specifically, during the examination stage, the patient is placed in a predetermined position. Subsequently, the user activates the data acquisition component to generate the medical data of the patient.

In step 430, a post examination stage of the DAP is performed. In particular, the medical data obtained during step 420 is processed and stored in the memory 220. In addition, the operational data 600 is generated and stored in the memory 220.

Figure 6:
FIG. 6 show operational data, according to exemplary embodiments.

FIG. 6. shows a sample record of the operational data 600, which may include a Serial Reference Number (SRN) 601, a utilization error 602, a time/date stamp 603, a technician ID 604 and environmental data 605. Those skilled in the art would understand that other fields may be included in the operational data 600.

The SRN 601 may be used to identify the data acquisition component 230 and/or the MDAS 110. For example, the SRN 601 may be utilized to identify the data acquisition component's 230 manufacturer, a model number, a physical location within the system 100 and other identifying information of the data acquisition component 230 and/or the MDAS 110.

The utilization error 602 includes flaws, glitches, and any other faults that have occurred during the DAP. For example, with reference to the MRI device, the utilization errors may include a quenched magnet error, a quenched heater state magnet error, a low helium magnet error, a insufficient helium overpressure magnet error, a communication error, a patient table or support errors a system reboot, a system hang up, a system crash, a coil error, a system fast logon, a scan abort, a system hiccup, a system user recovered crash, a system start, a job completed failure, a auto-recovered crash, and a system conflict. Those skilled in the art would understand that in addition to the listed errors, other errors may also occur. A more specified embodiment for the utilization errors 602 will be described below with regard to FIG. 5.

The time/date stamp 603 records a time and a date of each utilization error 602 that occurred during the DAP. The technician ID 604 records the identification of the technician who performed the DAP using the MDAS 110. The environmental data 605 includes certain operational conditions of the data acquisition component 230 during the DAP at a time/date of the utilization error 602. Specifically, the environmental data 605 may relate to a temperature, a pressure, a moisture level and other environmental conditions in the location where the data acquisition component 230 is situated.

Returning to FIG. 4, in step 440, the MDAS 110 transmits the operational data 600 to the QRD System 160. The transmission of the operational data 600 may be done in response to a request from the QRD System 160 or the operational data may be transmitted automatically (e.g., based on a predetermined schedule).

In an alternative embodiment, the QRD System 160 may utilize a data mining process to retrieve the operational data 600 from the MDAS 110. The data mining process is the process of extracting data and summarizing it into useful information. For example, the QRD System 160 may utilize the data mining process via an ETL (Extract, Translate and Load) tool. The ETL tool would extract the operational data 600 from the MDAS 110, transform it for storing it in proper format and load it onto the memory 162. However, those skilled in the art would understand that "data mining" is a general term used to describe the process of extracting and transforming data and there are many methods of achieving this goal.

Figure 5:
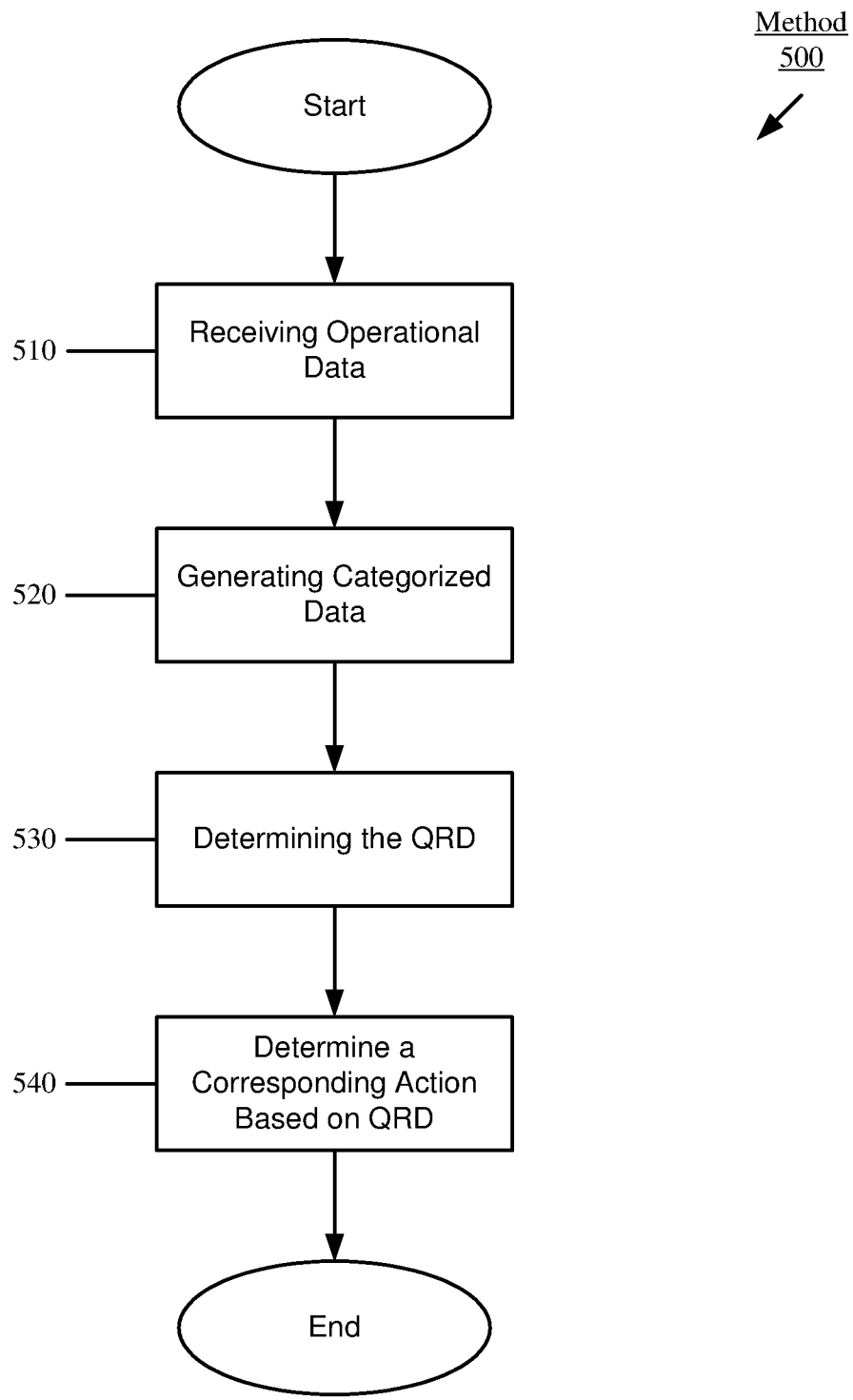
FIG. 5 shows a method for determining the QRD, according to exemplary embodiments.

FIG. 5 shows a method 500 for determining the QRD according to the exemplary embodiments. The method will be described with reference to the health care system 100 of FIG. 1. In step 510, the QRD System 160 receives the operational data 600 from the MDAS 110. As mentioned above, the operational data 600 is various data collected regarding the DAP.

In step 520, the QRD System 160 generates categorized data (e.g. second data) as a function of the operational data 600. The categorized data may be indicative of categories of the operational data 600. In particular, the processor 163 analyzes the utilization errors 602 and categorizes them. Each of the utilization errors 602 is assigned to a predetermined category. For example, the predetermined category is determined based on a number of factors, such as a severity of the utilization error 602.

In an exemplary embodiment, there may be the following four categories. Category 1 (L1) may include fatal utilization errors, such as data acquisition component 230 errors, communication errors and data acquisition component 230 shut down. L1 includes errors which would require the involvement of a professional repair service to fix the MDAS 100, which would force the cancellation of multiple possible DAPs.

In an exemplary embodiment, with reference to the MRI device, L1 may include the magnet errors, the patient table or support error, the system-wide fast reboot error, and the system-wide hang up error.

Category 2 (L2) may include major failure errors, such as, with reference to the MRI device, the system-wide crashes, the coil errors and the system-wide fast logon. L2 includes errors which would force a reboot of the data acquisition component 230 or repositioning of the patient.

Category 3 (L3) may include recoverable utilization errors, such as, with reference to the MRI device, the scan abort, the recon abort, the system-wide user recovered crash, the system-wide start, and the system wide job completed failure. L3 includes errors which are likely to disturb a workflow of the DAP for a short period of time.

Category 4 (L4) may include minor utilization errors, such as the automatically recovered crashes, the protocol definitions conflicts and the system-wide hiccup. L4 includes errors that hardly disturb the workflow of the DAP. Those skilled in the art would understand that the number of categories or location of the utilization error with regards to the category may be altered to increase accuracy and efficiency.

In step 530, the processor 163 determines the QRD as a function of the operational data 600, specifically the utilization errors 602, the categorized data and a corresponding coefficient of each category. The coefficient of each category may be predetermined. The QRD is be determined according to the following:

$$QRD = \frac{N}{\sum_{n=1}^{k} F_n L_n + F_{n+1} L_{n+1} + \ldots + F_k L_k}$$

Wherein: N=Total Number of MDAS Utilizations
F=Corresponding Category Coefficient
L=Number of Errors per Category
k=Total Number of Categories In an exemplary embodiment, the above equation is reduced to the embodiment below where the QRD may be defined by the formula:

$$QRD=N/(F_1*L_1+F_2*L_2+F_3*L_3+F_4*L_4)$$

Wherein: $F_1$=0.5 $L_1$=Number of L1 Utilization Errors
$F_2$=0.35 $L_2$=Number of L2 Utilization Errors
$F_3$=0.01 $L_3$=Number of L3 Utilization Errors
$F_4$=0.006 $L_4$=Number of L4 Utilization Errors Initially, the corresponding coefficients may be determined on a trial and error basis. For example, one hundred and fifty (150) utilizations from the plurality of MDASs 110, 120 may be analyzed and the corresponding coefficients determined. The plurality of MDASs 110, 120 would need to be similar in function, such as the plurality of MDASs 110, 120 would only contain MRI devices or only CT devices. Those skilled in the art would understand that different corresponding coefficients may be set for each of a different type of the plurality of MDASs 110 120 (e.g. MRI devices, CT devices). Alternatively, the corresponding coefficients may be revised in real-time after each MDAS 110 utilization. This enables the corresponding coefficients to be adjusted on an accumulating number of prior MDAS 110 utilizations.

In an exemplary embodiment, the corresponding coefficient may be determined by the QRD System 160 utilizing a neural network type computational model. The neural network is an information-processing paradigm able to extract patterns and detect trends. Specifically, the neural network may analyze the user's response to the utilization errors 602 from the plurality of similar MDASs 110, 120 and periodically adjust the corresponding coefficient. Those skilled in the art would understand that the neural network may analyze other factors in adjusting the corresponding coefficient.

In step 540, the processor 163 may determine the corresponding action based on the QRD. In an exemplary embodiment, the QRD is compared to a predetermined threshold range. Those skilled in the art would also understand that a plurality of threshold ranges may be used and each threshold may be correlated to a different corresponding action. The threshold range is a bounds of two numbers correlated to the corresponding action. Therefore, if the QRD is determined to be within the threshold range, the corresponding action is be engaged.

Specifically, the corresponding action may be an action of transmitting instructions to the MDAS 110 which would recommend that the data acquisition component 230 be shut down. In the alternative, the processor 163 may remotely shut down the data acquisition component 230, in real-time, to prevent the MDAS 110 from sustaining damage.

Further, the QRD System 160 may have a system-wide control over the plurality of MDASs 110, 120. The processor 163 may distinguish between the plurality of MDASs 110, 120 from operational data 600, specifically, from the SRN 601.

Those skilled in the art would understand that the corresponding action may also include issuing a maintenance recommendation, rebooting the MDAS 110, recommending repositioning the patient, scheduling a maintenance, recommending replacement of the data acquisition component 230, running a diagnostic test, adjust components of the data acquisition component 230 or other corresponding actions.

The QRD may be utilized as a reliability metric to evaluate and compare a performance of the plurality of MDASs 110, 120. For example, with reference to the MRI device, its manufacturer may compare the QRD of its device to the QRD of other MRI devices. This would show a potential customer how the manufacturer's MRI device compares to other MRI devices.

The QRD system 160 may be utilized in product service by providing system-wide diagnostic information and enabling control over specific aspects of the plurality of MDASs 110, 120. For example, if the QRD for the MDAS 110 falls into a certain threshold range, an alert may be issued on the QRD System 160, specifically, on the output device 164. An operator of the QRD System 160 may access the operational data 600 of that specific MDAS 110 and see the plurality of utilization errors 602 relating to a certain component of the data acquisition component 230. The operator may then either transmit an alert to the MDAS 110 and recommend replacing the certain component or the operator may remotely shut down the data acquisition component 230 until the certain component is fixed.

Alternatively, the operator may access the operation data 600 and see that a disproportionate amount of the utilization errors 602 occurred in the presence of a certain MDAS 110 technician. The operator may then issue a recommendation that the certain MDAS 110 technician receive additional training before utilizing the MDAS 110 again. This would improve workflow by reducing the time spent performing the DAP.

The QRD system 160 may also be utilized in product development and manufacturing of the data acquisition component 230 and its parts. For example, the manufacturer of the data acquisition component 230 may use the real-time data to see which parts fail and how often, which would enable the manufacturer to engineer better parts based on the failure rate and to ensure that the parts are in adequate stock for possible upcoming repairs. Further, this would increase the repair rate of the data acquisition component 230, which would result in less downtime and an improved workflow of the MDAS 110. Thus, there is improved customer satisfaction and a decreased cost of operation of the MDAS 110.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

We claim:

1. A method for determining a quality rating data (QRD) of a medical data acquisition system (MDAS), comprising:
   receiving first data which includes utilization errors by the MDAS that occurred while performing a data acquisition procedure (DAP) to acquire medical data by a data acquisition component of the MDAS;
   generating second data based on a function of the first data, the second data being indicative of categories of the utilization errors, wherein at least one utilization error is assigned to a corresponding category of the categories of the utilization errors based on a predetermined parameter;
   determining the quality rating data based on a function of a total number of MDAS utilizations, a corresponding coefficient for the corresponding category of the categories of the utilization errors and a number of utilization errors in the corresponding category of the categories of the utilization errors; and
   determining a corresponding action based on a function of the QRD.

2. The method of claim 1, wherein the quality rating data (QRD) is determined according to the following:

$$QRD = \frac{N}{\sum_{n=1}^{k} F_n L_n + F_{n+1} L_{n+1} + \ldots + F_k L_k}$$

wherein N is the total number of the MDAS utilizations; Fn is the coefficient corresponding to the utilization error categories, Ln is a number of utilization errors in the error category, and k is a total number of the utilization error categories.

3. The method of claim 1, wherein the MDAS includes one of a magnetic resonance imagining device, a computed tomography device, an ultrasound device, an X-ray device, and a nuclear magnetic resonance device.

4. The method of claim 1, wherein the utilization error categories includes at least one of:
- a category L1, which contains fatal utilization errors;
- a category L2, which contains major utilization errors;
- a category L3, which contains recoverable utilization; and
- a category L4, which contains minor utilization errors.

5. The method of claim 1, wherein a corresponding coefficient of F1 is 0.5, a corresponding coefficient of F2 is 0.35, a corresponding coefficient of F3 is 0.01, and a corresponding coefficient of F4 is 0.006.

6. The method of claim 1, wherein the first data further includes at least one of a serial reference number of the data acquisition component 230 or the MDAS, a time/date stamp of the utilization error that occurred during the data acquisition procedure, an identification number of a technician who performed the data acquisition procedure using the MDAS, and environmental data of the data acquisition component during the data acquisition procedure at a time/date of the utilization error.

7. The method of claim 1, wherein the corresponding action includes at least one of:
- transmitting instructions to the MDAS;
- remotely shutting down the data acquisition component;
- issuing a maintenance recommendation;
- rebooting the MDAS;
- scheduling a maintenance;
- recommending a replacement of the data acquisition component;
- running a diagnostic test on the data acquisition component; and
- adjusting components of the data acquisition component.

8. The method of claim 1, wherein the receiving further includes utilizing a data mining process to retrieve the first data.

9. The method of claim 1, wherein the corresponding coefficient includes being determined by utilizing a neural network type computational model.

10. A system for determining a quality rating data (QRD) of a medical data acquisition system (MDAS), comprising:
- a memory configured to receive first data which includes utilization errors by the MDAS that occurred while performing a data acquisition procedure (DAP) to acquire medical data by a data acquisition component of the MDAS;
- a processor configured to generate second data based on a function of the first data, the second data being indicative of categories of the utilization errors, wherein at least one utilization error is assigned to a corresponding category of the categories of the utilization errors based on a predetermined parameter,
- wherein the processor is configured to determine the quality rating data based on a function of a total number of MDAS utilizations, a corresponding coefficient for the corresponding category of the categories of the utilization errors and a number of utilization errors in the corresponding category of the categories of the utilization errors; and
- wherein the processor is configured to determine a corresponding action based on a function of the QRD.

11. The system of claim 10, wherein the quality rating data (QRD) is determined according to the following:

$$QRD = \frac{N}{\sum_{n=1}^{k} F_n L_n + F_{n+1} L_{n+1} + \ldots + F_k L_k}$$

wherein N is the total number of the MDAS utilizations; Fn is the coefficient corresponding to the utilization error categories, Ln is a number of utilization errors in the error category, and k is a total number of the utilization error categories.

12. The system of claim 10, wherein the MDAS includes one of a magnetic resonance imagining device, a computed tomography device, an ultrasound device, an X-ray device, and a nuclear magnetic resonance device.

13. The system of claim 10, wherein the utilization error categories includes at least one of:
- a category L1, which contains fatal utilization errors;
- a category L2, which contains major utilization errors;
- a category L3, which contains recoverable utilization; and
- a category L4, which contains minor utilization errors.

14. The system of claim 10, wherein a corresponding coefficient of F1 is 0.5, a corresponding coefficient of F2 is 0.35, a corresponding coefficient of F3 is 0.01, and a corresponding coefficient of F4 is 0.006.

15. The system of claim 10, wherein the first data further includes at least one of a serial reference number of the data acquisition component or the MDAS, a time/date stamp of the utilization error that occurred during the data acquisition procedure, an identification number of a technician who performed the data acquisition procedure using the MDAS, and environmental data of the data acquisition component during the data acquisition procedure at a time/date of the utilization error.

16. The system of claim 10, wherein the corresponding action includes at least one of:
- transmitting instructions to the MDAS;
- remotely shutting down the data acquisition component;
- issuing a maintenance recommendation;
- rebooting the MDAS;
- scheduling a maintenance;
- recommending a replacement of the data acquisition component;
- running a diagnostic test on the data acquisition component; and
- adjusting components of the data acquisition component.

17. The system of claim 10, wherein the first data is received based on utilizing a data mining process to retrieve the first data.

18. The system of claim 10, wherein the corresponding coefficient includes being determined by utilizing a neural network type computational model.

19. A system for determining a quality rating data of a medical data acquisition system (MDAS), comprising:
- a memory configured to store a program and to receive first data which includes utilization errors by the MDAS that occurred while performing a data acquisition procedure to acquire medical data by a data acquisition component of the MDAS;
- a processor configured to execute the program stored in the memory, wherein, when executed by the processor, the program causes the system to perform a process that includes:
- generating second data as based on function of the first data, the second data being indicative of categories of the utilization errors, wherein at least one utilization error is assigned to a corresponding category of the categories of the utilization errors based on a predetermined parameter;
- determining the quality rating data as based on function of a total number of MDAS utilizations, a corresponding coefficient for the corresponding category of the categories of the utilization errors and a number of utilization errors in the corresponding category of the categories of the utilization errors, and determining a corresponding action based on a function of the quality rating data (QRD), wherein the utilization error categories includes at least one of:

a category L1, which contains fatal utilization errors;
a category L2, which contains major utilization errors;
a category L3, which contains recoverable utilization; and
a category L4, which contains minor utilization errors.

20. The system of claim 19, wherein the corresponding action includes at least one of:

remotely shutting down the data acquisition component;
rebooting the MDAS;
running a diagnostic test on the data acquisition component; and
adjusting components of the data acquisition component.

* * * * *